United States Patent [19]
Yeh

[11] Patent Number: 5,649,942
[45] Date of Patent: Jul. 22, 1997

[54] SURGICAL INSTRUMENT

[76] Inventor: Charles Yeh, 5370 NW. 35 Ter., Ft. Lauderdale, Fla. 33309

[21] Appl. No.: 581,454

[22] Filed: Dec. 29, 1995

[51] Int. Cl.$^6$ .................................................. A61B 17/22
[52] U.S. Cl. ........................... 606/160; 606/51; 606/162
[58] Field of Search ............................... 606/51, 52, 61, 606/160, 161, 162, 166, 91

[56] References Cited

U.S. PATENT DOCUMENTS

| | | | |
|---|---|---|---|
| 1,628,275 | 4/1927 | Robinson | 606/161 |
| 2,677,843 | 5/1954 | Goodman | 606/160 |
| 5,348,023 | 9/1994 | McLucas | 606/160 |

*Primary Examiner*—Michael Buiz
*Assistant Examiner*—Kevin Truong
*Attorney, Agent, or Firm*—Dressler, Rockey, Milnamow & Katz, Ltd.

[57] ABSTRACT

A disposable comedone extractor for use in dermatologic surgery fabricated of a synthetic resin reinforced with natural or synthetic fibers. It has been found that the use of a reinforced synthetic resin ensures that the extractor of the present invention is fully disposable, and thus far less expensive to manufacture and use, as compared to conventional extractors fabricated from metals. In addition, the use of a synthetic resin allows greater control of the flexibility of the extractor as compared to rigid metal extractors.

6 Claims, 1 Drawing Sheet

SURGICAL INSTRUMENT

BACKGROUND OF THE INVENTION

This invention relates to an improved surgical device, and particularly an improved comedone extractor for use in dermatologic surgery.

As is well understood by those skilled in the art, a number of devices particularly well suited for use in dermatologic surgery have come into widespread acceptance. One of those devices is referred to as a Schamberg comedone extractor widely used by dermatologists in acne surgery. Such devices include an elongate shaft and, on each end of the shaft, have a tool configured for dermatologic surgery. The typical surgical comedone extractor has integrally formed in one end a fenestrated cup configuration used to isolate a dermatologic lesion by pressing down on the shaft with the fenestrated cup encircling the lesion to isolate the lesion from surrounding tissue. For example, acne lesions can be lanced by isolating the lesion. The opposite end of the conventional extractor includes what has become known as a crimped loop. That end of the tool is sometimes used for engaging portions of the lesion for removal.

In the past, comedone extractors have been fabricated from metals, and typically surgical steels. The use of such metals in the fabrication of comedone extractors constitute a number of disadvantages. In the first place, such extractors formed of metals are expensive, and thus cannot be economically considered disposable. That in turn requires dermatologists to sterilize the instruments, adding to the cost and inconvenience of their use. In addition, it is more difficult to accurately control the pressure applied to dermatologic lesions using comedone extractors fabricated from metals. Such metals tend to have excessive rigidity which detracts from their use in many dermatologic procedures.

It is accordingly an object of the present invention to provide a comedone extractor which overcomes the foregoing disadvantages.

It is a more specific objective of the present invention to provide a comedone extractor which is fabricated from a flexible reinforced plastic which not only allows the extractor to be disposable, but allows a dermatologic surgeon to more accurately control the pressure applied to lesions in the use of such extractors.

It is yet a further objective of the invention to provide a comedone extractor for use in dermatologic surgery in which the extractor is fabricated from a fiber-reinforced plastic to ensure disposability and to more accurately control the flexibility of such extractors when used in dermatologic procedures.

These and other objectives and advantages of the invention will appear more fully hereinafter from the following description of the invention.

SUMMARY OF THE INVENTION

The concepts of the present invention reside in a comedone extractor formed of a elongate shaft and having surgical tools positioned on the ends thereof which has been fabricated from a fiber-reinforced plastic. It has been found that the use of fiber-reinforced plastics in the fabrication of such surgical tools not only ensures their being disposable, but also allows a greater degree of control over the flexibility of the surgical tool. As a result, a dermatologic surgeon has greater control over the pressures applied in the use of the extractor of the present invention as compared to prior art devices having the same configuration but fabricated from metal.

In accordance with the preferred practice of the invention, use can be made of a variety of thermoplastic and thermosetting plastics which are reinforced with either natural or synthetic fibers. In the preferred embodiment of the invention, the extractor of the invention is fabricated from a polymer which may be a polyamide such as nylon, vinyl polymers based on vinyl chloride, styrene, acrylonitrile and combinations thereof (such as polyvinyl chloride, polystyrene, acrylonitrilebutadiene-styrene copolymers and the like), polyolefins such as polypropylene, polycarbonates, polyesters, polyacetals and the like which have been reinforced with fibers such as glass fibers, carbon fibers, polymeric fibers (e.g., dacron, aramid and other organic fiber-forming polymers) and the like. The extent of the fiber reinforcement can be varied within wide ranges as is well understood in the art of fiber-reinforced plastics. In general, good results are obtained when the fibers are present in an amount ranging from 15 to 50% by weight based on total weight of the composite.

DETAILED DESCRIPTION OF THE INVENTION

Figure 1:
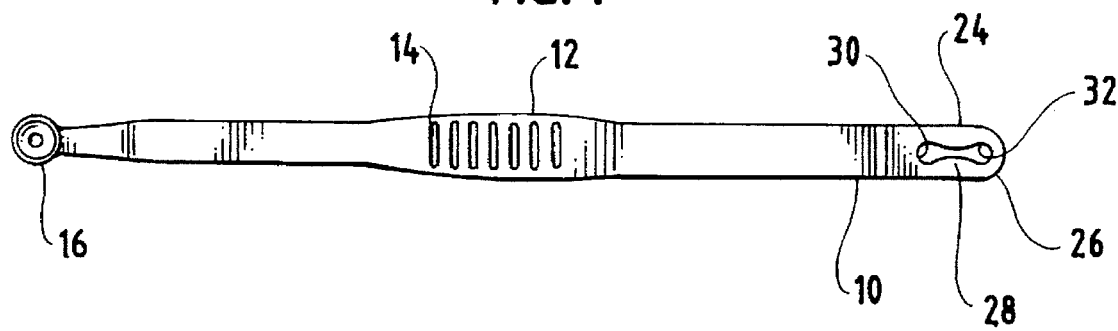
FIG. 1 is a top view and elevation of a comedone extractor embodying the features of the present invention.
Figure 2:
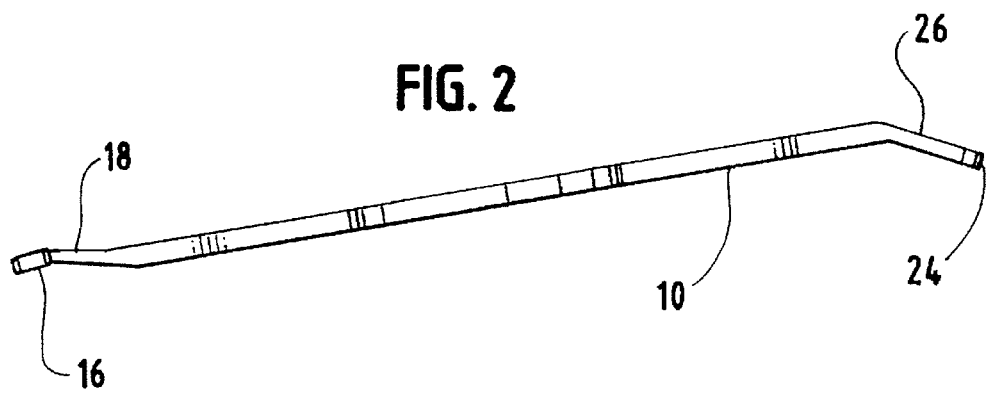
FIG. 2 is a side view in elevation of the comedone extractor illustrated in FIG. 1.
Figure 3:
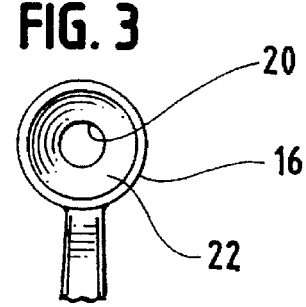
FIG. 3 is a view of the fenestrated cup configuration utilized on one end of the comedone extractor illustrated in FIG. 1.

The comedone extractor of the present invention is illustrated in FIGS. 1–3 of the drawing, and has a conventional configuration including an elongated body portion 10 having an expanded center portion 12 having a plurality of ridges 14 on both surfaces thereof serving as a grip for the dermatologist. Positioned at one end is a fenestrated cup tool portion 16 integral with the elongated body portion 10. As is perhaps best shown in FIG. 2, the fenestrated cup tool portion 14 is mounted integral with an angular portion 18 of the body 10. By positioning the fenestrated cup tool portion at an angle relative to the elongate shaft, the cup of the tool is more readily used in certain areas of the anatomy, particularly in the areas of the nose and the ears.

As is perhaps best illustrated in FIG. 3, the fenestrated cup portion 16 has a central opening 20 extending therethrough and a curved cup surface 22 forming the body of the fenestrated cup configuration. The opposite end of the body portion 10 includes a crimped loop portion 24 mounted on a second angular portion 26. As is illustrated in FIG. 1 of the drawing, the loop 26 constitutes an opening extending through the body portion and having a neck portion 28 which is narrowed between loops 30 and 32.

As will be appreciated by those skilled in the art, a number of tool elements can be mounted on the elongate shaft, formed integral therewith, apart from the fenestrated cup tool portion and the crimped loop portions described by way of illustration of the present invention. For example, it is possible to employ tool portions consisting of scalpels and other loop configurations which are themselves well known to those skilled in the art.

The comedone extractor of the present invention is, as noted above, fabricated from one of a number of plastic materials described above. In general, such plastics are thermoplastic and thermosetting polymeric resins having low modulus and a low degree of rigidity sufficient to allow the comedone extractor to be used in isolating tissue samples for dermatologic surgery. It has been found that the improved flexibility of dermatologic tools according to the present invention formed of reinforced plastics cause substantially less bruising when employed in dermatologic surgery as compared to the corresponding instruments fabricated from metals such as steel.

Suitable polymers used in the practice of the present invention include polyamide and like polymers described above. Preferred for use in the practice of the present invention are polyamide such as nylon or acrylonitrile-butadiene-styrene copolymers which have been reinforced with 15 to 50%, and preferably 25 to 35%, by weight of fiber reinforcement. For that purpose, use can be made of a number of fibers selected from the group of natural and synthetic fibers. Good results have been achieved using glass fibers and preferably glass fibers which have been chopped to short length. In the fabrication of the comedone extractor of the present invention, the chopped fibers are blended with the polymer in accordance with conventional techniques employed in the art of fiber reinforced plastics and then the comedone extractor of the invention is molded, again using conventional molding techniques.

It has been found that the use of such nylon and acrylonitrile-butadiene-styrene polymers reinforced with chopped glass fibers provide a comedone extractor which is not only disposable, but also allows the comedone extractor of the invention to be used by a dermatologist with greater control over the flexibility of the surgical tool.

It will be understood that various changes and modifications can be made in the details of construction, procedure and use without departing from the spirit of the invention, especially as defined in the following claims.

What is claimed is:

1. A disposable comedone extractor for use in dermatologic surgery comprising an elongate body portion, a cup configuration tool positioned at one end of the body portion and another dermatologic tool positioned at the other end of the body ports, with the tool and the cup configuration being formed integral with the elongate body portion and each being dispositioned at an angle with respect thereto, said extractor fabricated from a synthetic resin reinforced with natural or synthetic fibers.

2. An extractor as defined in claim 1 wherein the resin is a polyamide resin.

3. An extractor as defined in claim 1 wherein the resin is an acrylonitrile-butadiene-styrene copolymer.

4. An extractor as defined in claim 1 wherein the fibers are glass fibers.

5. An extractor as defined in claim 1 wherein the cup configuration tool has a fenestrated cup configuration.

6. An extractor as defined in claim 1 wherein the dermatologic tool is a crimped loop tool.

* * * * *